United States Patent [19]

Yamamoto et al.

[11] 4,228,167
[45] Oct. 14, 1980

[54] DIURETIC AND VASODILATING TRICYCLIC QUINAZOLINES

[75] Inventors: Michihiro Yamamoto; Masao Koshiba, both of Nishinomiya; Shunji Aono, Toyonaka, all of Japan

[73] Assignee: Sumitomo Chemical Company, Limited, Osaka, Japan

[21] Appl. No.: 939,869

[22] Filed: Sep. 5, 1978

[30] Foreign Application Priority Data

Sep. 6, 1977 [JP] Japan .................. 52/107643

[51] Int. Cl.² ............... A61K 31/505; C07D 487/14
[52] U.S. Cl. ............................... 424/251; 544/250
[58] Field of Search ..................... 544/250; 424/251

[56] References Cited

U.S. PATENT DOCUMENTS

| | | | |
|---|---|---|---|
| 3,932,407 | 1/1976 | Beverung, Jr. et al. | 544/247 X |
| 3,957,819 | 5/1976 | White | 260/326.15 |
| 3,976,645 | 8/1976 | White | 544/252 |
| 3,984,556 | 10/1976 | Hardtmann | 424/251 |
| 4,126,683 | 11/1978 | White et al. | 424/251 |

FOREIGN PATENT DOCUMENTS

2508543 9/1975 Fed. Rep. of Germany ........... 544/252

OTHER PUBLICATIONS

Zderic, et al., Chemical Abstracts, vol. 55, 8472e (1960).

Migrdichian, Organic Synthesis, vol. 1, p. 580, Reinhold Publishing Corp., New York (1957).

Fuson, Reactions of Organic Compounds, John Wiley & Sons, New York, pp. 648–652 (1964).

*Primary Examiner*—Donald G. Daus
*Assistant Examiner*—Diana G. Rivers
*Attorney, Agent, or Firm*—Stevens, Davis, Miller & Mosher

[57] ABSTRACT

Novel imidazo[2,1-b]quinazolines and pyrimido-[2,1-b]quinozolines represented by the formula,

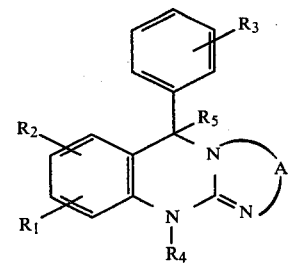

wherein $R_1$, $R_2$, $R_3$, $R_4$, $R_5$ and A are as defined in the specification were prepared. They have prominent pharmacological properties such as diuretic and vasodilating activity.

6 Claims, No Drawings

DIURETIC AND VASODILATING TRICYCLIC QUINAZOLINES

This invention relates to novel tricyclic quinazolines and processes for preparation thereof.

More particularly, the present invention pertains to imidazo[2,1-b]quinazolines and pyrimido[2,1-b]quinazolines having useful pharmacological activities.

The compounds of the present invention are represented by the formula,

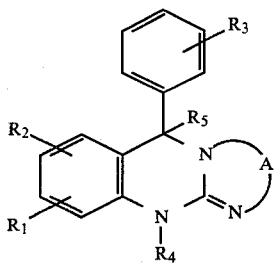

(I)

wherein $R_1$, $R_2$ and $R_3$ are independently hydrogen, halogen, $C_{1-3}$ alkyl or $C_{1-3}$ alkoxy; $R_4$ is $C_{1-5}$ alkyl, $C_{3-5}$ alkenyl, aralkyl or cyclo $C_{3-8}$ alkyl-$C_{1-3}$ alkyl; $R_5$ is hydrogen or hydroxy; and A is $C_{2-3}$ alkylene which may be optionally substituted by one or two $C_{1-3}$ alkyl.

In the compounds of the above formula (I) and elsewhere in the specification, the term "alkyl" means both straight- and branched-chain saturated aliphatic hydrocarbon radicals, and the $C_{1-5}$ alkyl may be methyl, ethyl, n-propyl, isopropyl, n-butyl, isobutyl, tert-butyl or n-pentyl; the $C_{1-3}$ alkoxy may be methoxy, ethoxy, n-propoxy or isopropoxy. The term "$C_{3-5}$ alkenyl" includes, for example, allyl, 2- and 3-butenyl. The term "aralkyl" means aryl substituted $C_{1-3}$ alkyl wherein the aryl moiety is phenyl or halogen substituted phenyl. The term "cyclo $C_{3-8}$ alkyl" includes cyclopropyl, cyclobutyl, cyclopentyl, cyclohexyl, cycloheptyl and cyclooctyl. The term "halogen" includes all four halogens, preferably chlorine and bromine. The term "$C_{2-3}$ alkylene" in the symbol A, which may optionally have one or two $C_{1-3}$ alkyl radicals, includes, for example, ethylene, propylene, 1,1-dimethylethylene, 1,2-dimethylethylene, 1-ethylethylene, 1-(n-propyl)ethylene and trimethylene.

This invention also includes addition salts of the compounds of the formula (I) formed with pharmaceutically acceptable acids. Such acids include both organic and inorganic acids, for example, hydrochloric, hydrobromic, hydroiodic, sulfuric, phosphoric, acetic, oxalic, maleic, fumaric, succinic, tartaric, citric, ascorbic, glutamic, aspartic, stearic and palmitic acids.

The novel tricyclic quinazolines represented by the formula (I) possess prominent pharmacological properties. In particular, these compounds have diuretic and vasodilating activity and are useful in the treatment of cardiovascular diseases.

Diuretic activity was evaluated according to the method described by W. L. Lipschits et al., J. Pharmacol. Exp. Ther., 79, 97 (1943). The results in rats are shown in Table I, where the data for a standard dose of 10 mg/kg is listed for the purpose of comparison.

TABLE I

| Compound of the formula (I) | | | | | | Urinary excretion | | | |
|---|---|---|---|---|---|---|---|---|---|
| | | | | | | | mequiv/kg | | |
| $R_1$ | $R_2$ | $R_3$ | $R_4$ | $R_5$ | A | ml/kg | $Na^{30}$ | $K^{30}$ | $Na^+/K^+$ |
| 7-Cl | H | H | n-Bu | H | $CH_2CH_2$ | 31.1 | 4.5 | 0.86 | 5.3 |
| 8-Cl | H | H | $CH_2$—⊲ | H | $CH_2CH_2$ | 26.8 | 3.7 | 0.92 | 4.0 |
| 8-Cl | H | H | Me | H | $CH_2CH_2CH_2$ | 38.3 | 5.6 | 0.97 | 5.6 |
| 9-Cl | H | H | $CH_2$—⊲ | H | $CH_2CH_2CH_2$ | 34.3 | 4.7 | 0.78 | 6.1 |
| H | H | p-Cl | Me | OH | $CH_2CH_2$ | 32.6 | 4.4 | 0.84 | 5.2 |
| Control | | | | | | 9.5 | 1.5 | 0.53 | 2.9 |

Vasodilating activity was examined by use of the method described by N. Tada et al., J. Pharmacol. Exp. Ther., 191, 139 (1974). The rat aortic strips were isolated and contracted using 30 mM of potassium chloride. Dose dependent relaxation in the aortic strips was observed by adding the test compounds. At the end of each experiment, papaverine in a concentration of $3 \times 10^{-5}$ g/ml was added and the relaxation induced was taken as 100%. Median effective concentration ($ED_{50}$) was obtained from dose response curves. The results are shown in Table II.

TABLE II

| Compound of the formula (I) | | | | | | $ED_{50}$ |
|---|---|---|---|---|---|---|
| $R_1$ | $R_2$ | $R_3$ | $R_4$ | $R_5$ | A | |
| 8-Cl | H | H | $CH_2$—⊲ | H | $CH_2CH_2$ | $2.4 \times 10^{-7}$ g/ml |
| 7-MeO | H | H | $CH_2$—⊲ | H | $CH_2CH_2$ | $1 \times 10^{-6}$ |
| 8-Cl | H | H | n-Bu | H | $CH_2CH_2CH_2$ | $2.7 \times 10^{-7}$ |
| 9-Cl | H | H | $CH_2$—⊲ | H | $CH_2CH_2CH_2$ | $2.9 \times 10^{-7}$ |
| Papaverine | | | | | | $4.6 \times 10^{-6}$ |

For purposes of administration to warm-blooded animals, the compounds of the invention can be combined with solid or liquid pharmaceutical carriers and formulated in the form of tablets, powder packets, capsules and the like solid dosage forms, dissolved or suspended in suitable solvents or vehicles for enteral or parenteral administration.

According to the present invention tricyclic quinazolines of the formula (I) may be prepared by the following methods.

One method for synthesis of the compounds of the formula,

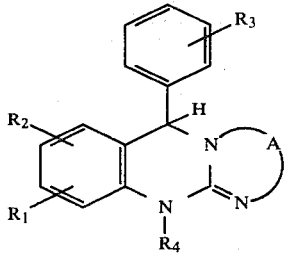 (Ia)

wherein $R_1$, $R_2$, $R_3$, $R_4$ and A are as defined above, comprises reacting a compound of the formula,

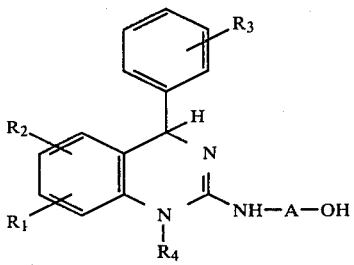 (II)

wherein $R_1$, $R_2$, $R_3$, $R_4$ and A are as defined above, with phosphorus oxychloride, followed by an alkali.

The reaction of the compound of the formula (II) with phosphorus oxychloride may be carried out at an elevated temperature in the presence or absence of an inert solvent. The reaction is conveniently effected by refluxing in excess phosphorus oxychloride, and, if necessary, an inert solvent such as benzene, toluene, xylene, chloroform and ethylene dichloride may be employed. After removal of unreacted phosphorus oxychloride by distillation, the residue is basified with an alkali such as sodium hydroxide, potassium hydroxide, sodium carbonate, potassium carbonate or ammonia water to yield the objective compound of the formula (Ia).

The starting compound of the formula (II) can be prepared by heating a compound of the formula,

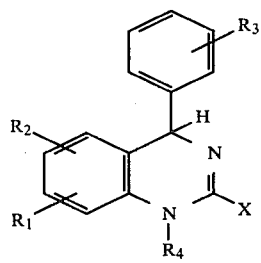 (III)

wherein $R_1$, $R_2$, $R_3$, and $R_4$ are as defined above; and X is methylthio or halogen, with an amino alcohol of the formula,

 (IV)

wherein A is as defined above.

Another method for synthesis of the compounds of the formula (Ia), comprises treating a compound of the formula,

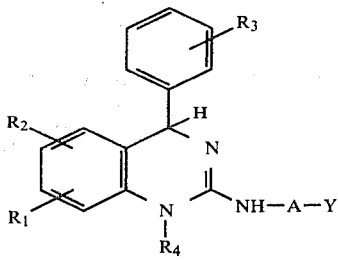 (V)

wherein $R_1$, $R_2$, $R_3$, $R_4$ and A are as defined above; and Y is halogen, with an alkali in an inert solvent. Suitable alkalies include sodium hydroxide, potassium hydroxide, sodium carbonate, potassium carbonate, ammonia water and the like. Solvents that may be used include methanol, ethanol, isopropanol, tetrahydrofuran, acetone, benzene, toluene and the like.

The starting compounds of the formula (V) can be prepared by reacting a compound of the aforesaid formula (II) with thionyl chloride, phosphorus trichloride, phosphorus tribromide, phosphorus oxychloride or the like.

A further method for synthesis of the compounds of the formula (I) comprises reacting a compound of the formula,

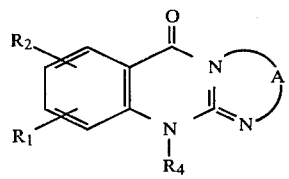 (VI)

wherein $R_1$, $R_2$, $R_4$ and A are as defined above, with an organometallic compound of the formula,

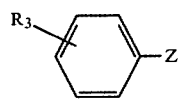 (VII)

wherein $R_3$ is as defined above; and Z is lithium or $MgX'$ (wherein $X'$ is halogen), in an inert solvent, followed by the reaction with water, to yield a compound of the formula,

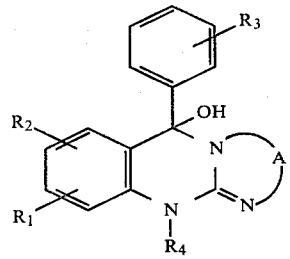 (Ib)

wherein $R_1$, $R_2$, $R_3$, $R_4$ and A are as defined above, and further reacting the thus obtained compound (Ib) with a reducing agent which may be used for hydrogenolysis of tertiary alcohols.

The reaction of the first step may be carried out at a temperature in the range of from room temperature to the boiling point of the solvent employed. Suitable solvents include diethyl ether, dimethoxyethane, diethylene glycol dimethyl ether, tetrahydrofuran, dioxane and the like.

The reduction may be, for example, effected by non-noble metal in an alcohol or an acid (e.g., zinc and hydrochloric acid and sodium and alcohol), catalytic hydrogenation over Raney nickel or palladium on charcoal, or sodium borohydride and trifluoroacetic acid which is described by G. W. Gribble et al., Synthesis, 1977, 172.

According to the present invention, there are obtained, for example, the following novel imidazo[2,1-b]quinazolines and pyrimido[2,1-b]quinazolines.

7-Chloro-10-methyl-5-phenyl-2,3,5,10-tetrahydroimidazo[2,1-b]quinazoline
8-Chloro-10-methyl-5-phenyl-2,3,5,10-tetrahydroimidazo[2,1-b]quinazoline
8-Chloro-10-ethyl-5-phenyl-2,3,5,10-tetrahydroimidazo[2,1-b]quinazoline
8-Chloro-10-(n-propyl)-5-phenyl-2,3,5,10-tetrahydroimidazo[2,1-b]quinazoline
8-Chloro-10-isopropyl-5-phenyl-2,3,5,10-tetrahydroimidazo[2,1-b]quinazoline
7-Chloro-10-(n-butyl)-5-phenyl-2,3,5,10-tetrahydroimidazo[2,1-b]quinazoline
8-Chloro-10-(n-butyl)-5-phenyl-2,3,5,10-tetrahydroimidazo[2,1-b]quinazoline
9-Chloro-10-(n-butyl)-5-phenyl-2,3,5,10-tetrahydroimidazo[2,1-b]quinazoline
8-Chloro-10-(isobutyl)-5-phenyl-2,3,5,10-tetrahydroimidazo[2,1-b]quinazoline
8-Chloro-10-(n-pentyl)-5-phenyl-2,3,5,10-tetrahydroimidazo[2,1-b]quinazoline
8-Methyl-10-(n-butyl)-5-phenyl-2,3,5,10-tetrahydroimidazo[2,1-b]quinazoline
7-Methoxy-10-(n-butyl)-5-phenyl-2,3,5,10-tetrahydroimidazo[2,1-b]quinazoline
8-Chloro-7-methyl-10-(n-butyl)-5-phenyl-2,3,5,10-tetrahydroimidazo[2,1-b]quinazoline
7,8-Dimethyl-10-(n-butyl)-5-phenyl-2,3,5,10-tetrahydroimidazo[2,1-b]quinazoline
10-Allyl-5-phenyl-2,3,5,10-tetrahydroimidazo[2,1-b]quinazoline
10-Allyl-8-chloro-5-phenyl-2,3,5,10-tetrahydroimidazo[2,1-b]quinazoline
10-Benzyl-8-chloro-5-phenyl-2,3,5,10-tetrahydroimidazo[2,1-b]quinazoline
8-Chloro-10-(p-fluorobenzyl)-5-phenyl-2,3,5,10-tetrahydroimidazo[2,1-b]quinazoline
9-Chloro-10-cyclopropylmethyl-5-phenyl-2,3,5,10-tetrahydroimidazo[2,1-b]quinazoline
10-Cyclopropylmethyl-7,8-dimethoxy-5-phenyl-2,3,5,10-tetrahydroimidazo[2,1-b]quinazoline
9-Chloro-10-cyclohexylmethyl-5-phenyl-2,3,5,10-tetrahydroimidazo[2,1-b]quinazoline
8-Chloro-10-cyclopentylmethyl-5-phenyl-2,3,5,10-tetrahydroimidazo[2,1-b]quinazoline
8-Chloro-10-cyclohexylmethyl-5-(p-chlorophenyl)-2,3,5,10-tetrahydroimidazo[2,1-b]quinazoline
5-(p-Chlorophenyl)-10-methyl-2,3,5,10-tetrahydroimidazo[2,1-b]quinazoline
9-Chloro-11-methyl-6-phenyl-3,4,6,11-tetrahydro-2H-pyrimido[2,1-b]quinazoline
9-Chloro-11-(n-butyl)-6-phenyl-3,4,6,11-tetrahydro-2H-pyrimido[2,1-b]quinazoline
10-Chloro-11-(n-butyl)-6-phenyl-3,4,6,11-tetrahydro-2H-pyrimido[2,1-b]quinazoline
8-Chloro-11-cyclopropylmethyl-6-phenyl-3,4,6,11-tetrahydro-2H-pyrimido[2,1-b]quinazoline
8-Chloro-11-cyclopropylmethyl-6-(o-chlorophenyl)-3,4,6,11-tetrahydro-2H-pyrimido[2,1-b]quinazoline
9-Bromo-11-cyclopropylmethyl-6-phenyl-3,4,6,11-tetrahydro-2H-pyrimido[2,1-b]quinazoline
11-Cyclopropylmethyl-6-(p-tolyl)-3,4,6,11-tetrahydro-2H-pyrimido[2,1-b]quinazoline
7-Chloro-5-hydroxy-10-methyl-5-phenyl-2,3,5,10-tetrahydroimidazo[2,1-b]quinazoline
8-Chloro-5-hydroxy-10-ethyl-5-phenyl-2,3,5,10-tetrahydroimidazo[2,1-b]quinazoline
8-Chloro-5-hydroxy-10-(n-propyl)-5-phenyl-2,3,5,10-tetrahydroimidazo[2,1-b]quinazoline
8-Chloro-5-hydroxy-10-(n-butyl)-5-phenyl-2,3,5,10-tetrahydroimidazo[2,1-b]quinazoline
8-Chloro-10-cyclopropylmethyl-5-hydroxy-5-phenyl-2,3,5,10-tetrahydroimidazo[2,1-b]quinazoline
8-Chloro-10-cyclohexylmethyl-5-hydroxy-5-phenyl-2,3,5,10-tetrahydroimidazo[2,1-b]quinazoline
10-Allyl-8-chloro-5-hydroxy-5-phenyl-2,3,5,10-tetrahydroimidazo[2,1-b]quinazoline
9-Chloro-11-(n-butyl)-5-hydroxy-5-phenyl-3,4,6,11-tetrahydro-2H-pyrimido[2,1-b]quinazoline The following examples are given by way of illustration and are not to be construed as limitations of this invention.

EXAMPLE 1

To a suspension of 7.6 g of 6-chloro-3,4-dihydro-1-(n-butyl)-4-phenyl-(2(1H)-quinazolinethione in 80 ml of methanol were added 4.9 g of methyl iodide. The mixture was heated under reflux for 2 hours and then cooled with ice. The resulting precipiate was collected by filtration, washed with methanol and dried to give 10 g of 6-chloro-1,4-dihydro-1-(n-butyl)-2-methylthio-4-phenylquinazoline hydroiodide, m.p. 203° C. (decomp.).

A mixture of 6.15 g of the thus obtained quinazoline hydroiodide and 10 ml of monoethanolamine was heated with stirring at 110°–120° C. for 5 hours. After cooling, the mixture was poured into ice-water, and the resulting mixture was extracted with chloroform. The chloroform layer was washed with water, dried over anhydrous sodium sulfate and evaporated under reduced pressure. The residue was chromatographed on silica gel using a mixture of chloroform and methanol (15:1, V/V) as an eluent to give 4.6 g of 6-chloro-1,4-dihydro-2-($\beta$-hydroxyethylamino)-1-(n-butyl)-4-phenylquinazoline as a light brown oil.

Finally, a mixture of the whole oily product above obtained and 15 ml of phosphorus oxychloride was heated under reflux for 1 hour, cooled and then poured into ice-water. The resulting mixture was basified with ammonia water and extracted with chloroform. The chloroform layer was washed with water, dried over anhydrous sodium sulfate, and concentrated to dryness under reduced pressure. The residue was chromatographed on silica gel using chloroform as an eluent to yield 3.2 g of 7-chloro-10-(n-butyl)-5-phenyl-2,3,5,10-tetrahydroimidazo[2,1-b]quinazoline as a light brown oil, which was crystallized from n-hexane to give colorless prisms, m.p. 97°–97.5° C.

EXAMPLE 2

According to substantially the same procedure as that of Example 1, there were obtained the following 2,3,5,10-tetrahydroimidazo[2,-b]quinazoline derivatives from the corresponding starting compounds.

7-Chloro-10-methyl-5-phenyl-2,3,5,10-tetrahydroimidazo[2,1-b]quinazoline, m.p. 129°–129.5° C.

7-Chloro-10-isopropyl-5-phenyl-2,3,5,10-tetrahydroimidazo[2,1-b]quinazoline, light yellow oil.

7-Chloro-10-cyclopropylmethyl-5-phenyl-2,3,5,10-tetrahydroimidazo[2,1-b]quinazoline hydrochloride. ½ isopropyl alcohol, m.p. 291°–292° C. (decomp.).

8-Chloro-10-cyclopropylmethyl-5-phenyl-2,3,5,10-tetrahydroimidazo[2,1-b]quinazoline hydrochloride, m.p. 301°–302° C.

9-Chloro-10-cyclopropylmethyl-5-phenyl-2,3,5,10-tetrahydroimidazo[2,1-b]quinazoline, light brown oil.

10-Cyclopropylmethyl-7-methoxy-5-phenyl-2,3,5,10-tetrahydroimidazo[2,1-b]quinazoline hydrochloride, m.p. 265.5°–266° C. (decomp.).

10-(n-Butyl)-5-phenyl-2,3,5,10-tetrahydroimidazo[2,1-b]quinazoline hydrochloride, m.p. 297° C. (decomp.).

EXAMPLE 3

To a suspension of 14.2 g of 6-chloro-3,4-dihydro-1-methyl-4-phenyl-2(1H)-qinazolinethione in 140 ml of methanol were added 7.68 g of methyl iodide. The mixture was heated under reflux for 3 hours and then concentrated. After cooling with ice, the precipitate was collected by filtration, washed with methanol, and dried to give 20.5 g of 6-chloro-1,4-dihydro-1-methyl-2-methylthio-4-phenylquinazoline hydroiodide, m.p. 196°–197° C. (decomp.).

A mixture of 4.31 g of the thus obtained quinazoline hydroiodide and 15 ml of n-propanolamine was heated at 100° C. for 2 hours.

After cooling, isopropyl ether was added to the mixture and the resulting precipitate was collected by filtration. The crystals were then dissolved in chloroform, and the solution was washed successively with dilute ammonia water and water, dried over anhydrous sodium sulfate and concentrated to dryness under reduced pressure. The residue was crystallized from chloroform-isopropyl ether to give 3.1 g of 6-chloro-1,4-dihydro-2-(γ-hydroxypropylamino)-1-methyl-4-phenylquinazoline, m.p. 165°–166° C.

A mixture of 2.85 g of the thus obtained 2-(γ-hydroxypropylamino)quinazoline and 10 ml of phosphorus oxychloride was heated under reflux for 3 hours. After removal of unreacted phosphorus oxychloride under reduced pressure, the residue was basified with ammonia water with ice-cooling. The mixture was then extracted with chloroform and the chloroform layer was washed with water, dried over anhydrous sodium sulfate and concentrated to dryness under reduced pressure. The residual brown oil was chromatographed on activated alumina using chloroform as an eluent to give 2.7 g of 8-chloro-11-methyl-6-phenyl-3,4,6,11-tetrahydro-2H-pyrimido[2,1-b]quinazoline. The product was then dissolved in methanolic hydrogen chloride and the solvent was evaporated under reduced pressure. The residue was recrystallized from methanol-isopropyl ether to give the hydrochloride of the product as colorless prisms, m.p. 257.5°–258° C. (decomp.).

EXAMPLE 4

According to substantially the same procedure as that of Example 3, there were obtained the following 3,4,6,11-tetrahydro-2H-pyrimido[2,1-b]quinazoline derivatives from the corresponding 3,4-dihydro-2(1H)-quinazolinethione derivatives.

8-Chloro-11-(n-butyl)-6-phenyl-3,4,6,11-tetrahydro-2H-pyrimido[2,1-b]quinazoline hydrochloride, m.p. 273°–274° C. (decomp.).

9-Chloro-11-cyclopropylmethyl-6-phenyl-3,4,6,11-tetrahydro-2H-pyrimido[2,1-b]quinazoline hydrochloride, m.p. 276°–277° C. (decomp.).

EXAMPLE 5

A mixture of 3.3 g of 6-chloro-1,4-dihydro-2-(γ-hydroxypropylamino)-1-methyl-4-phenylquinazoline, 3.6 g of thionyl chloride and 50 ml of chloroform was stirred at room temperature overnight, and refluxed for an additional 2 hours. The reaction mixture was concentrated to dryness under reduced pressure to give 3.5 g of 6-chloro-1,4-dihydro-2-(γ-chloropropylamino)-1-methyl-4-phenylquinazoline as a residue. To the residue were added 100 ml of dry ethanol and 2.8 g of potassium carbonate and the resulting mixture was heated under reflux for 5 hours. After cooling, insoluble material was filtered off and the filtrate was concentrated to dryness. The residue was chromatographed on activated alumina using chloroform as an eluent to give 8-chloro-11-methyl-6-phenyl-3,4,6,11-tetrahydro-2H-pyrimido[2,1-b]quinazoline.

EXAMPLE 6

To a phenylmagnesium bromide solution prepared from 6.9 g of p-chlorophenyl bromide, 0.88 g of magnesium and 25 ml of dry diethyl ether was added dropwise a solution of 2.42 g of 10-methyl-2,3,5,10-tetrahydroimidazo[2,1-b]quinazoline-5-one in 30 ml of dry tetrahydrofuran with stirring and ice-cooling. The mixture was heated under reflux for 2 hours and then cooled. To the mixture were added dropwise 20 ml of water and stirring was continued for a while. The resulting mixture was extracted with hot chloroform and the insoluble material was filtered off and washed with hot chloroform. The chloroform layer was dried over anhydrous sodium sulfate and concentrated to dryness under reduced pressure. The residue was crystallized from ethanol and the crystals were further recrystallized from dimethylformamide to give 1.0 g of 5-(p-chlorophenyl)-5-hydroxy-10-methyl-2,3,5,10-tetrahydroimidazo[2,1-b]quinazoline as colorless needles, m.p. 207°–209° C. (decomp.).

EXAMPLE 7

According to substantially the same procedure as that of Example 6, there were obtained the following compounds.

5-Hydroxy-10-methyl-5-phenyl-2,3,5,10-tetrahydroimidazo[2,1-b]quinazoline, m.p. 213°–215° C. (decomp.).

10-Ethyl-5-hydroxy-5-phenyl-2,3,5,10-tetrahydroimidazo[2,1-b]quinazoline, m.p. 194°–195° C. (decomp.).

10-Benzyl-5-hydroxy-5-phenyl-2,3,5,10-tetrahydroimidazo[2,1-b]quinazoline, m.p. 181°–182° C. (decomp.).

10-Allyl-5-hydroxy-5-phenyl-2,3,5,10-tetrahydroimidazo[2,1-b]quinazoline, m.p. 169°–171° C. (decomp.).

10-(n-Butyl)-5-hydroxy-5-phenyl-2,3,5,10-tetrahydroimidazo[2,1-b]quinazoline, m.p. 175°–176° C. (decomp.).

8-Chloro-5-hydroxy-10-methyl-5-phenyl-2,3,5,10-tetrahydroimidazo[2,1-b]quinazoline, m.p. 196°–197° C. (decomp.).

6-Hydroxy-11-methyl-6-phenyl-3,4,6,11-tetrahydro-2H-pyrimido[2,1-b]quinazoline, m.p. 222°–224° C. (decomp.).

EXAMPLE 8

To 20 ml of trifluoroacetic acid were added portionwise with stirring both of 0.48 g of 5-hydroxy-10-(n-butyl)-5-phenyl-2,3,5,10-tetrahydroimidazo[2,1-b]quinazoline and 0.57 g of sodium borohydride below 0° C. under nitrogen. The reaction mixture was stirred at 0°–5° C. for 1 hour and the trifluoroacetic acid was evaporated under reduced pressure. To the residue were added 20 ml of ice-water and then 15 ml of 40% sodium hydroxide solution. After stirring for a while, the mixture was extracted with chloroform and the chloroform layer was washed with water, dried over anhydrous sodium sulfate and concentrated under reduced pressure. The residue was chromatographed on silica gel using chloroform as an eluent to give 0.3 g of 10-(n-butyl)-5-phenyl-2,3,5,10-tetrahydroimidazo[2,1-b]quinazoline as a light yellow oil. An ethanol solution of the product was treated with ethanolic hydrogen chloride and evaporated under reduced pressure. The residue was recrystallized from ethanol to give colorless prisms (hydrochloride), m.p. 297° C. (decomp.).

EXAMPLE 9

According to substantially the same procedure as that of Example 8, there were obtained the following compounds.

8-Chloro-10-cyclopropylmethyl-5-(p-chlorophenyl)-2,3,5,10-tetrahydroimidazo[2,1-b]quinazoline hydrochloride. isopropyl alcohol, m.p. 319°–320° C. (decomp.).

10-(p-Fluorobenzyl)-5-phenyl-2,3,5,10-tetrahydroimidazo[2,1-b]quinazoline hydrochloride, m.p. 283.5°–284.5° C.

8-Chloro-11-(n-butyl)-6-phenyl-3,4,6,11-tetrahydro-2H-pyrimido[2,1-b]quinazoline hydrochloride, m.p. 273°–274° C. (decomp.).

What is claimed is:

1. A compound of the formula,

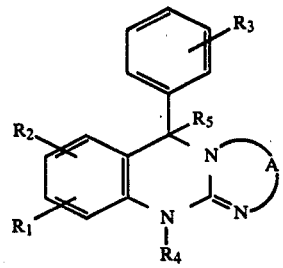

(I)

wherein $R_1$, $R_2$ and $R_3$ are independently hydrogen, halogen, $C_{1-3}$ alkyl or $C_{1-3}$ alkoxy; $R_4$ is $C_{1-5}$ alkyl, $C_{3-5}$ alkenyl, aralkyl or cyclo $C_{3-8}$ alkyl-$C_{1-3}$ alkyl; $R_5$ is hydrogen or hydroxy; and A is $C_{2-3}$ alkylene which may optionally be substituted by one or two $C_{1-3}$ alkyl, or a pharmaceutically acceptable acid addition salt thereof.

2. A compound according to claim 1, wherein $R_5$ is hydrogen.

3. A compound according to claim 1, wherein $R_5$ is hydroxy.

4. A compound according to claim 1 wherein either $R_1$ or $R_3$ is halogen, $C_{1-3}$ alkyl or $C_{1-3}$ alkoxy.

5. A compound according to claim 4, wherein A is ethylene or trimethylene.

6. A pharmaceutical composition comprising as an active ingredient a diuretically or vasodilatingly effective amount of a compound of claim 1, or its pharmaceutically acceptable acid addition salts and a pharmaceutically acceptable carrier.

* * * * *